(12) United States Patent
Green et al.

(10) Patent No.: US 6,734,190 B2
(45) Date of Patent: May 11, 2004

(54) DIHYDRODIPYRAZOLOPYRIDINYLBENZAMIDE AND -SULFONAMIDE INHIBITORS OF B7-1

(75) Inventors: Neal Jeffrey Green, Newton, MA (US); Jason Shaoyun Xiang, Winchester, MA (US); Audrey Molina Davies, Arlington, MA (US); Lihren Chen, Cambridge, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/629,276

(22) Filed: Jul. 28, 2003

(65) Prior Publication Data

US 2004/0024008 A1 Feb. 5, 2004

Related U.S. Application Data

(60) Provisional application No. 60/399,146, filed on Jul. 29, 2002.

(51) Int. Cl.[7] ..................... A61K 31/437; C07D 471/12
(52) U.S. Cl. .......................................... 514/293; 546/82
(58) Field of Search ............................. 514/293; 546/82

(56) References Cited

U.S. PATENT DOCUMENTS 3,669,950 A    6/1972  Hoehn et al.
4,560,689 A   12/1985  Yokoyama
4,814,450 A    3/1989  Yokoyama

OTHER PUBLICATIONS

Erbe, D. V.; Wang, S.; Xing, Y.; and Tobin, J.F.; The Journal of Biological Chemistry (2002), vol. 277, 7363–7368.
Ian T. Forbes et al., Journal of Medicinal Chemistry, 1990, vol. 33, 2640–2645.

*Primary Examiner*—Charanjit S. Aulakh
(74) *Attorney, Agent, or Firm*—Barbara L. Lences

(57) ABSTRACT

The present invention provides a compound of formula I and the use thereof for the immunotherapeutic treatment of transplant rejection or autoimmune disease.

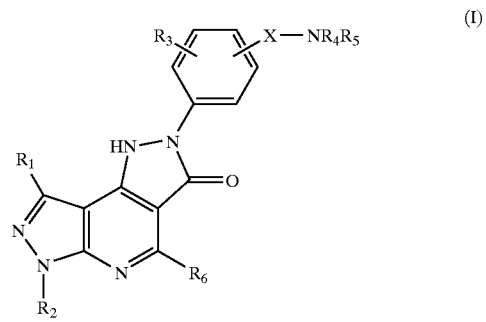

20 Claims, No Drawings

DIHYDRODIPYRAZOLOPYRIDINYLBENZAMIDE AND -SULFONAMIDE INHIBITORS OF B7-1

This application claims priority from copending provisional application Ser. No. 60/399,146, filed Jul. 29, 2002, the entire disclosure of which is hereby incorporated by reference.

BACKGROUND OF THE INVENTION

Regulation of T cell responses plays a primary role in determining the outcome of auto-immune disease, the development of tumor immunity, and graft survival following transplantation (Bluestone, et. al. *Annu, Rev. Immunol.* 1996, 14, 233–258.; Kuchroo, et. al. *Crit. Rev. Immunol.* 1998, 18, 389418.; Guinan, et. al. *N. Engl. J. Med.* 1999, 340, 1704–1714.; Abrams et. al. *J. Exp. Med.* 2000, 192, 681–694). These immune responses are controlled by the interaction of molecules on T cell and antigen presenting cell surfaces. Activation of T cells requires two signals, an antigen-specific signal delivered through T cell antigen receptor, and a second co-stimulatory signal. This co-stimulatory signal dictates the outcome for T cells through the binding of B7-1 and B7-2 expressed on antigen presenting cells to CD28 and CTLA-4 on T cells. CD28 engagement by B7-1 or B7-2 amplifies T cell receptor signaling and stimulates production of cytokines required for T-cell proliferation. On the other hand, CTLA-4 engagement by B7-1 or B7-2 down regulates the immune response (Allison, et. al. *Nature* 1992, 356, 607–609.; Bluestone, et. al. *Immunity* 1994, 1, 405–413.; Thompson, et. al. *Science* 1995, 270, 985–988). In experimental disease models, altering these co-stimulatory signals has profound effects on immunity. Blocking B7/CD28 interactions with monoclonal antibodies or soluble receptors results in immunosuppression and enhanced allograft survival, while B7/CTLA-4 blockade results in enhanced ant-tumor immune responses (Larsen, et. al. *Nature* 1996, 381, 434–438). Consequently, agents, such as small molecules, which act as inhibitors of cell-cell interactions may be useful in the development of effective immunomodulatory medicines.

Therefore, it is an object of this invention to provide compounds which are useful as immunotherapeutic agents in the treatment of transplant rejection, autoimmune disease or graft vs host disease.

It is another object of this invention to provide therapeutic methods and pharmaceutical compositions useful for the treatment of transplant rejection, autoimmune disease or graft vs host disease.

It is a feature of this invention that the compounds provided may be used to further study and elucidate the interactions of B7-1 with the CD28 receptor.

These and other objects and features of the invention will become more apparent by the detailed description set forth hereinbelow.

SUMMARY OF THE INVENTION

The present invention provides a compound of formula I

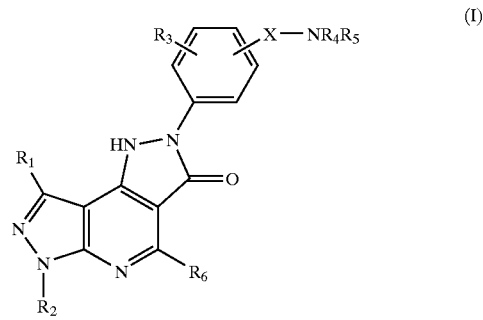

wherein

X is CO or $SO_2$;

$R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;

$R_3$ is H, F, Cl, Br or I;

$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group, phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group, benzyl optionally substituted with one or two halogen, $OR_{14}$, $COR_{18}$, or a $C_1$–$C_3$alkyl group optionally substituted with one $OR_{14}$ group, or pyridinyl optionally substituted with one or two halogen, $OR_{14}$, $NR_{15}R_{16}$ or $CO_2R_{17}$ groups, or $R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;

$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;

$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;

n is 0 or an integer of 1 or 2;

$R_{14}$ is H, $C_1$–$C_3$alkyl or $C_1$–$C_3$haloalkyl;

$R_{19}$ is H or $C_1$–$C_3$alkyl; and $R_{20}$ is a $C_1$–$C_6$alkyl, $C_3$–$C_7$cycloalkyl, $C_1$–$C_6$haloalkyl, phenyl, $C_5$–$C_7$cyloheteroalkyl or heteroaryl group each optionally substituted; or the stereoisomers thereof or the pharmaceutically acceptable salts thereof.

The present invention also provides methods and compositions useful for the immunotherapeutic treatment of transplant rejection, autoimmune disease or graft vs host disease.

DETAILED DESCRIPTION OF THE INVENTION

Full T cell activation requires both an antigen-specific and a second co-stimulatory signal. Co-stimulation dictates the outcome for T cells through the binding of B7-1 and B7-2 expressed on antigen-presenting cells to CD28 and CTLA-4 on T cells (Greenfield, E. A., Nguyen, K. A. and Kuchroo, V. K. (1998) Critical Review of Immunology, 18, 389–418 and Lenschow, D. J., Walunas, T. L. and Bluestone, J. A. (1996) Annual Review of Immunology, 14, 233–258). Animal studies and clinical trials with protein antagonists of these interactions indicate considerable promise for immunotherapy in transplantation and autoimmune disease.

Surprisingly, it has now been found that dihydrodipyrazolopyridinylbenzamide and -sulfonamide compounds of formula I are effective inhibitors of B7-1/CD28 binding. Equilibrium dialysis demonstrates that compounds of formula I bind specifically to human B7-1 at a common site. Occupancy of this site by said inhibitors blocked B7-1 binding not only to CD28, but also to CTLA-4 (although at much higher concentrations of inhibitor). Accordingly, the present invention provides dihydrodipyrazolopyridinyl-benzamide or -sulfonamide B7-1 inhibitors of formula I

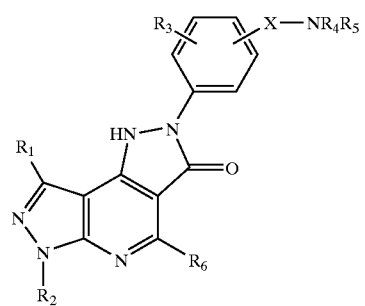

(I)

wherein

X is CO or $SO_2$;

$R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;

$R_3$ is H, F, Cl, Br or I;

$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group, phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group, benzyl optionally substituted with one or two halogen, $OR_{14}$, $COR_{18}$, or a $C_1$–$C_3$alkyl group optionally substituted with one $OR_{14}$ group, or pyridinyl optionally substituted with one or two halogen, $OR_{14}$, $NR_{15}R_{18}$ or $CO_2R_{17}$ groups, or $R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;

$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}$, $R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;

$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;

n is 0 or an integer of 1 or 2;

$R_{14}$ is H, $C_1$–$C_3$alkyl or $C_1$–$C_3$haloalkyl;

$R_{19}$ is H or $C_1$–$C_3$alkyl; and $R_{20}$ is a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted; or the stereoisomers thereof or the pharmaceutically acceptable salts thereof.

As used in the specification and claims, the term halogen designates F, Cl, Br or I and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein Z is NR, O or S; and R is H or an optional substituent as described hereinbelow:

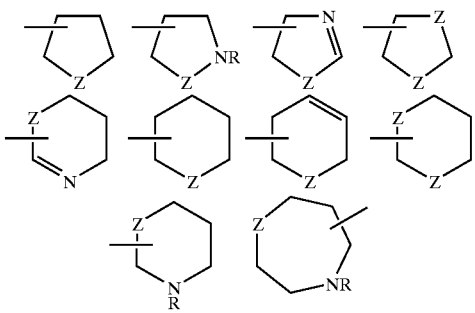

Similarly, as used in the specification and claims, the term heteroaryl designates a $C_5$–$C_{10}$ aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl or cycloalkyl groups, preferably halogen atoms, $NO_2$, $CF_3$ or OH groups. Typically, 0–3 substituents may be present, preferably 1 or 2. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, nitric, hydrochloric, hydrobromic, citric, malic, maleic, malonic, mandelic, succinic, fumaric, tartaric, propionic, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein X is CO. Also preferred are those compounds of formula I wherein $R_1$ is H. Another group of preferred compounds of formula I are those compounds wherein $R_6$ is a phenyl group optionally substituted with one or two halogen, CN, $NO_2$, $CF_3$, $C_1$–$C_3$alkoxy or $CO_2R_{23}$ groups.

More preferred compounds of the invention are those compounds of formula I wherein X is CO and $R_2$ is H or $C_1$–$C_3$alkyl. Another group of more preferred compounds are those compounds of formula I wherein X is CO and $R_4$ and $R_5$ are each independently H or a $C_1$–$C_3$alkyl, phenyl or benzyl group each optionally substituted with one or two hydroxy groups or $R_4$ and $R_5$ may be taken together with the atom to which they are attached to form a pyrrolidinyl or morpholinyl group each optionally substituted with one carboxy group. Further more preferred compounds of formula I are those compounds wherein X is CO; $R_1$ is H; $R_6$ is phenyl substituted in the 3-position with $CF_3$; and $R_2$ is H or $CH_3$.

Examples of the preferred compounds of formula I include:

N-(4-hydroxyphenyl)-3-(6-methyl-3-oxo-4-[3-(trifluoromethyl)phenyl]-3,6-dihydrodipyrazolo[3,4-b:3,4-d]pyridin-2(1H)-yl)benzamide;

N-(2,2-dimethoxyethyl)-N-methyl-3-(6-methyl-3-oxo-4-[3-(trfluoromethyl)phenyl]-3,6-dihydrodipyrazolo[3,4-b:3,4-d]pyridin-2(1H)-yl)benzamide;

6-methyl-2-[3-(1-pyrrolidinylcarbonyl)phenyl]-4-[3-(trifluoromethyl)phenyl]-1,6-dihydrodipyrazolo[3,4-b:3,4-d]pyridin-3(2H)-one;

(2R)-1-[3-(6-methyl-3-oxo-4-[3-(trifluoromethyl)phenyl]-3,6-dihydrodipyrazolo[3,4-b:3,4-d]pyridin-2(1H)-yl)benzoyl]-2-pyrrolidinecarboxylic acid;

N-(3,4-dihydroxybenzyl)-3-(6-methyl-3-oxo-4-[3-(trifluoromethyl)phenyl]-3,6-dihydrodipyrazolo[3,4-b:3,4-d]pyridin-2(1H)-yl)benzamide;

N-(2-hydroxypropyl)-3-(6-methyl-3-oxo-4-[3-(trifluoromethyl)phenyl]-3,6-dihydrodipyrazolo[3,4-b:3,4-d]-pyridin-2(1H)-yl)benzamide;

1-{2-chloro-5-[6-methyl-3-oxo-4-[3-(trifluoromethyl)pheny]-3,6-dihydrodipyrazolo[3,4-b:3',4'-d]pyridin-2(1H)-yl]benzoyl}-D-proline;

2-(4-chloro-3-{[(2R)-2-(hydroxymethyl)pyrrolidin-1-yl]carbonyl}phenyl)-6-methyl-4-[3-(trifluoromethyl)phenyl]-1,6-dihydrodipyrazolo[3,4-b:3,4-d]pyridin-3(2H)-one;

N-(4-hydroxyphenyl-4-{6-methyl-3-oxo-4-[3-(trifluoromethyl)phenyl]-3,6-dihydrodipyrazolo[3,4-b:3',4'-d]pyridin-2(1H)-yl}benzamide;

N-(2-hydroxyphenyl)-4-{6-methyl-3-oxo-3-[3-(trfluoromethyl)phenyl]-3,6-dihydrodipyrazolo[3,4-b:3',4'-d]pyridin-2(1H)-yl}benzamide;

6-methyl-2-[4-(4-morpholinylcarbonyl)phenyl]-4-[3-(trifluoromethyl)phenyl]-1,6-dihydrodipyrazolo[3,4-b:3,4-d]pyridin-3(2H)-one;

N-[4-(2-hydroxyethyl)phenyl]-4-(6-methyl-3-oxo-4-[3-(trifluoromethyl)phenyl1-3,6-dihydrodipyrazolo[3,4-b:3,4-d]pyridin-2(1H)-yl)benzamide;

N-[3-(1-hydroxyethyl)phenyl]-4-(6-methyl-3-oxo-443-(trifluoromethyl)phenyl]-3,6-dihydrodipyrazolo[3,4-b:3,4-d]pyridin-2(1H)-yl)benzamide;

N-[3-(hydroxymethyl)phenyl]4-(6-methyl-3-oxo-4-[3-(trifluoromethyl)phenyl]-3,6-dihydrodipyrazolo[3,4-b:3,4-d]pyridin-2(1H)-yl)benzamide;

N-(5-hydroxypentyl)-4-(6-methyl-3-oxo-4-[3-(trifluoromethyl)phenyl]-3,6-dihydrodipyrazolo[3,4-b:3,4-d]pyridin-2(1H)-yl)benzenesulfonamide;

N-benzyl-4-[6-methyl-3-oxo-4-(3-trifluoromethyl-phenyl)-3,6-dihydro-1H-1,2,5,6,7-pentaaza-as-indacen-2-yl]-benzenesulfonamide;

N-(2-hydroxyethyl)-4-(6-methyl-3-oxo-4-[3-(trifluoromethyl)phenyl]-3,6-dihydrodipyrazolo[3,4-b:3,4-d]pyridin-2(1H)-yl)benzenesulfonamide;

methyl ({[4-(6-methyl-3-oxo-4-[3-(trifluoromethyl)phenyl]-3,6-dihydrodipyrazolo[3,4-b:3,4-d]pyridin-2(1H)-yl)phenyl]sulfonyl}amino)acetate;

N-cyclopropylmethyl-4-[6-methyl-3-oxo-4-(3-trfluoromethyl-phenyl)-3,6-dihydro-1H-1,2,5,6,7-pentaaza-as-indacen-2-yl]-benzenesulfonamide;

({[4-(6-methyl-3-oxo-4-[3-(trifluoromethyl)phenyl]-3,6-dihydrodipyrazolo[3,4-b:3,4-d]pyridin-2(1H)-yl)phenyl]sulfonyl}amino)acetic acid;

the stereoisomers thereof; or the pharmaceutically acceptable salts thereof.

Advantageously, the present invention provides a process for the preparation of a compound of formula I wherein X is CO (Ia) which comprises reacting a compound of formula II with an amine, $HNR_4R_5$, in the presence of an activating agent such as dicyclohexylcarbodiimide (DCC) and a solvent. The reaction is shown in flow diagram I.

Flow Diagram I

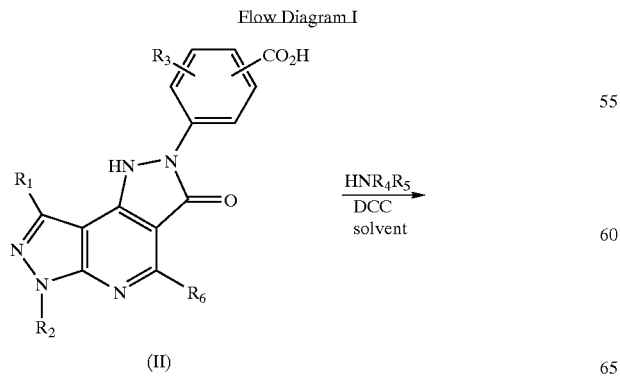

(II)

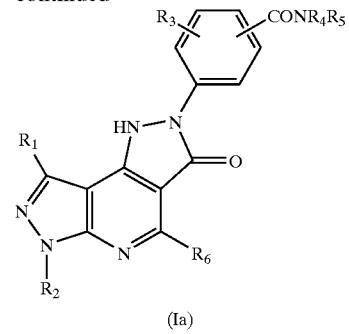

(Ia)

Activating agents suitable for use in the process of the invention include dicyclohexylcarbodimide, ethyidimethylaminocarbodimide, hydroxybenzotriaze or the like.

Solvents suitable for use in the process of the invention include polar solvents such as tetrahydrofuran, dimethyl formamide, dimethylsulfoxide or the like.

Compounds of formula I wherein X is $SO_2$ (Ib) may be prepared by protecting the sulfonamide of formula III to give the bis-protected compound of formula IV; alkylating the formula IV compound with the desired haloalkyl, $R_4$—X', in the presence of a base; and deprotecting the resultant alkylated formula IV compound optionally alkylating a second time with a haloalkyl, $R_5$—X', to give the desired sulfonamide of formula Ib. The reaction is shown in flow diagram II wherein P represents a protecting group such as t-butoxy carbonyl and X' represents Cl, Br or I.

Flow Diagram II

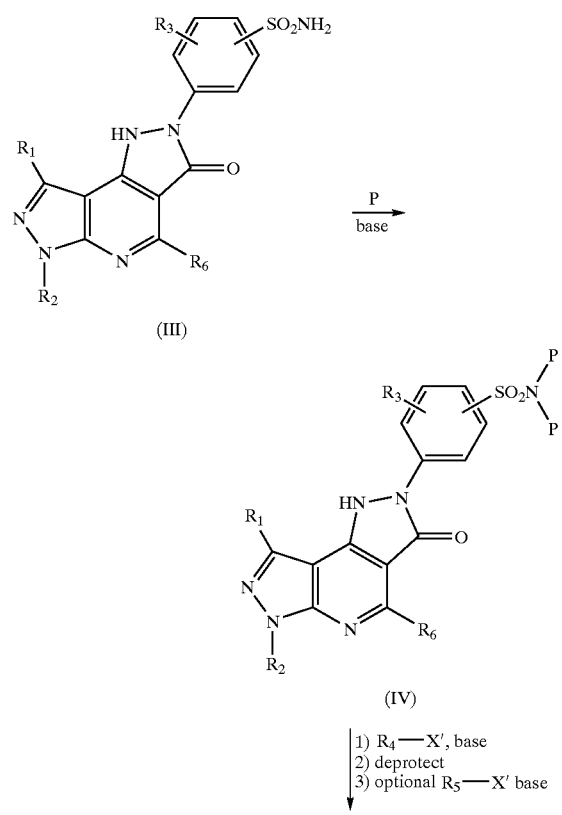

1) $R_4$—X', base
2) deprotect
3) optional $R_5$—X' base

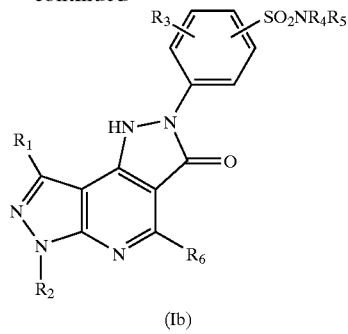

(Ib)

Protecting groups useful in the reactions described hereinabove include t-butyldicarboxylate, benzyl, acetyl, benzyloxycarbonyl, or any conventional group known to protect a basic nitrogen in standard synthetic procedures, preferably t-butyldicarboxylate.

Reaction conditions suitable for deprotection may vary according to the nature of the protecting group. For example, if the protecting group is t-butyl-carbonyl, deprotection takes place in the presence of an acid such as trifluoroacetic acid or HCL optionally in the presence of an aprotic solvent such as dioxane. If the protecting group is benzyl, deprotection takes place via hydrogenation in the presence of a catalyst, typically 10% Pd/carbon.

Compounds of formula II or III may be prepared using conventional synthetic methods and, if required, standard separation or isolation techniques.

For example, for compounds of formula V wherein W represents $CO_2H$ or $SO_2NH_2$; an aryl, heteroaryl or heterocycloalkyl ester of formula VI may undergo a Knoevenagel condensation to give the oxo ester for formula VII; said oxo ester is allowed to react with an aminopyrazole of formula VIII in the presence of a base to give the hydroxypyrazolopyridine of formula IX; said hydroxypyrazolopyridine is then converted to the corresponding chloro compound of formula X via reaction with a chlorinating agent such as thionyl chloride or phosphorous oxychloride; the resultant chloro compound may undergo an addition-elimination reaction with a hydrazine of formula XI to give the hydrazinyl intermediate of formula XII; and cyclization of the formula XII compound gives the desired intermediate of formula V. The reaction is illustrated in flow diagram III.

Flow Diagram III

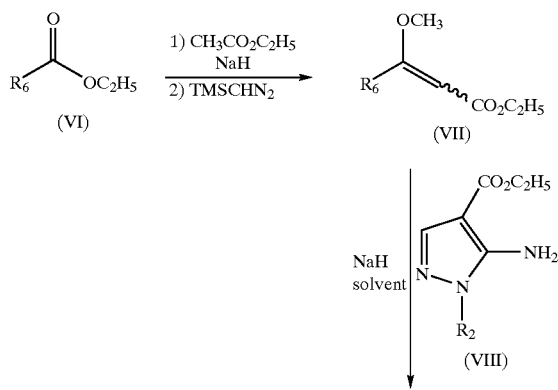

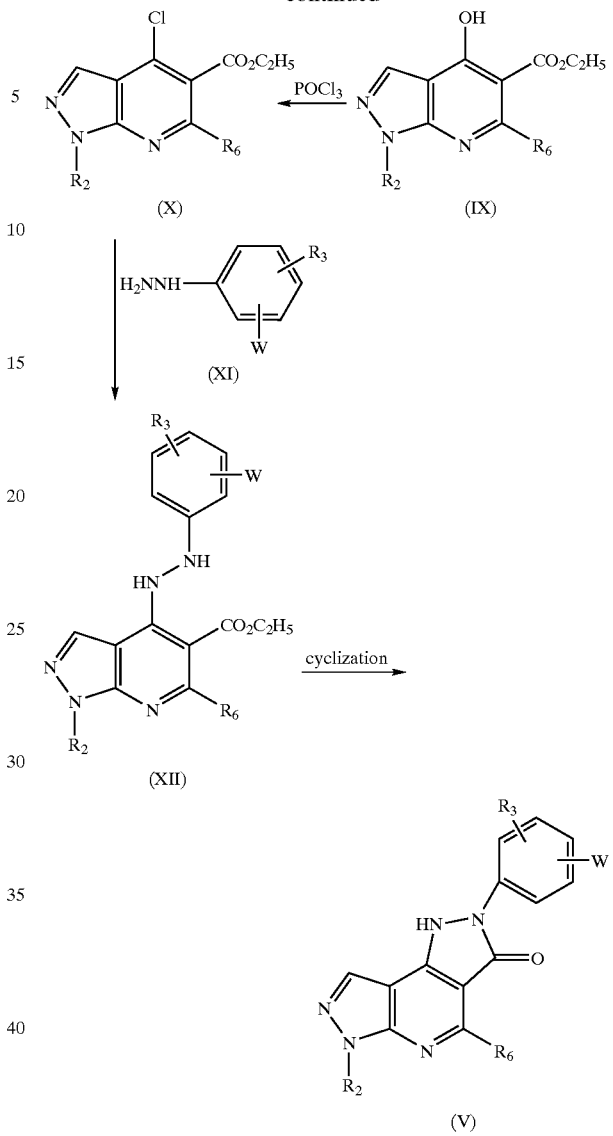

Cyclization of the intermediate of formula XII is accomplished in the presence of an acid, such as acetic acid, or a base, such as sodium methoxide or sodium hydride.

Advantageously, the compounds of formula I are useful for the treatment of immune disorders related to or affected by the immune regulatory protein B7-1 such as transplant rejection, graft vs host disease or an autoimmune disease such as multiple sclerosis, rheumatoid arthritis, diabetes mellitus, Grave's disease, pernicious anemia, myasthemia gravis, rheumatic fever, systemic lupus erythematosus, vitiligo, autoimmune Addison's disease, Hashimoto's thyroiditis, Crohn's disease or the like. Accordingly, the present invention provides a method for the treatment of an immune disorder related to or affected by the immune regulatory protein B7-1 which comprises providing a patent in need thereof with an immunotherapeutically effective amount of a compound of formula I as described hereinabove. The compounds may be provided by oral or parenteral administration or in any common manner known to be an effective administration of an immunotherapeutic agent to a patient in need thereof.

The term "providing" as used herein with respect to providing a compound or substance embraced by the invention, designates either directly administering such a compound or substance, or administering a prodrug, derivative or analogue which forms an equivalent amount of the compound or substance within the body.

The immunotherapeutically effective amount provided in the treatment of a specific immune disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula i as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula i. In tablets, the formula i compound may be mixed with a carrier having the necessary compression properties in suitable proportions and compacted in the shape and size desired. Said powders and tablets may contain up to 99% by weight of the formula i compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms EtOAc, THF and DMF designate ethyl acetate, tetrahydrofuran and dimethyl formamide, respectively. All chromatography is performed using $SiO_2$ as support

EXAMPLE 1

Preparation of Ethyl 3-Methoxy-3-[(trifluoromethyl)phenyl]-2-propenoate

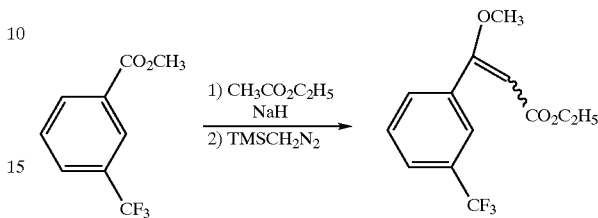

A solution of methyl 3-trifluoromethylbenzoate (62.0 g, 0.3 mol) in EtOAc is treated with NaH (60% in mineral oil, 8.4 g), and gently heated at 40° C. until a mild exotherm occurs. After the cessation of reflux, additional NaH is added (12.7 g, total of 0.6 mol) and the resultant mixture is heated at reflux temperature for 16 h, cooled to room temperature and diluted with methylene chloride and water. The organic phase is separated, washed with brine, dried over $Na_2SO_4$ and concentrated in vacuo to give an oil residue. The oil is treated with acetonitrile and methanol followed by a solution of $TMSCH_2N_2$ in hexanes (300 mL, 2M, 0.6 mol), stirred for 36 h and treated with aqueous 5% HCl. After nitrogen evolution ceases, the organic layer is separated, washed with brine, dried over $Na_2SO_4$ and concentrated in vacuo. The resultant residue is chromatographed through a plug of silica gel (4:1, hexanes: EtOAc) to give the title compound as a white solid, 65.5 g, (78% yield). This product is used as is in Example 2.

EXAMPLE 2

Preparation of Ethyl 4-Chloro-1-methyl-6-[3-(trifluoromethyl)phenyl-1H-pyrazolo[3,4-b]pyridine-5-carboxylate

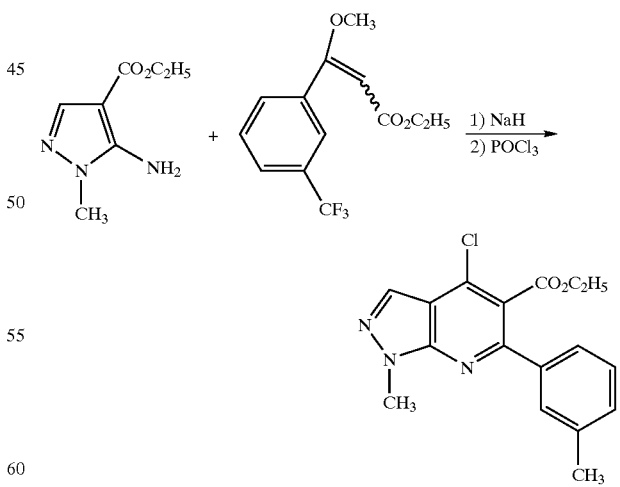

A solution of ethyl 5-amino-1-methyl-4-pyrazole carboxylate (42.2 g, 0.25 mol) in THF is treated with NaH (60% in mineral oil, 25.2 g, 0.75 mol), stirred for 30 min, treated with ethyl 3-methoxy-3-[(trifluoromethyl)phenyl]-2-propenoate (65.5 g, 0.25 mol), heated at reflux temperature for 36 h, cooled to 0° C., acidified to pH 5 with aqueous HCl and extracted with EtOAc. The extracts are combined, washed with brine, dried over $Na_2SO_4$ and concentrated in vacuo. The resultant off-white solid residue is triturated with hexanes to give a white solid. The solid is dissolved in phosphorus oxychloride (750 mL) and heated to reflux temperature for 2 h, cooled to room temperature and concentrated. This concentrate is dissolved in EtOAc, cooled to 0° C., and neutralized with aqueous $Na_2CO_3$. The organic phase is separated, washed with brine, dried over $Na_2SO_4$ and concentrated. This resultant residue is chromatographed on silica gel (3:1 hexanes:EtOAc) to afford the title compound as a white solid 65% (68% yield), characterized by HNMR and mass spectral analyses.

EXAMPLE 3

Preparation of 3-{6-Methyl-3-oxo-4-[3-(trifluoromethyl)phenyl]-3,6-dihydrodipyrazolo[3,4-b:3,4-d]pyridin-2(1H)-yl}benzoic acid

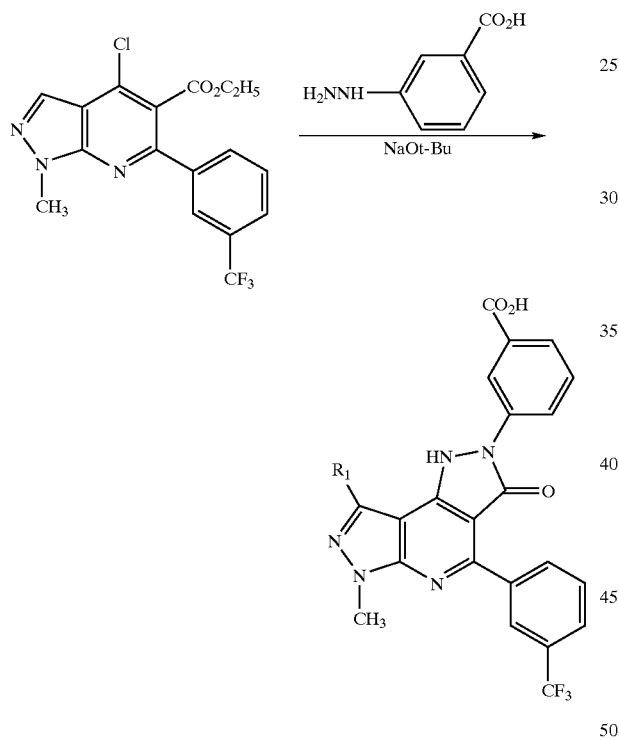

A solution of 3-hydrazinobenzoic acid (7.14 g, 0.047 mol) in ethylene glycol is treated with NaO-t-bu (4.5 g, 0.047 mol), stirred at 75° C. for 1 h, cooled to room temperature, treated with ethyl 4-chloro-1-methyl-6-(3-(trifluoromethyl)phenyl]-1H-pyrazolo[3,4-b]pyridine-5-carboxylate (6.0 g, 15.6 mmol), heated at 100° C. for 16 h, treated with additional NaO-t-bu (2.59, 0.026 mol), cooled to room temperature, diluted with water and EtOAc and acidified to pH 3 with 3N HCl. The phases are separated. The organic phase is dried over $Na_2SO_4$ and concentrated in vacuo. The resultant residue is triturated with 1.5:1 EtOAc:$CH_3OH$ at 65° C. for 1 h, stirred at room temperature for 3 h and filtered. The filtercake is washed with cold EtOAc and air-dried to afford the title product as a tan powder, 5.8 g (82% yield), mp 289–291° C., identified by HNMR and mass spectral analyses.

EXAMPLE 4

Preparation of 2-Chloro-5-hydrazinobenzoic acid Hydrochloride

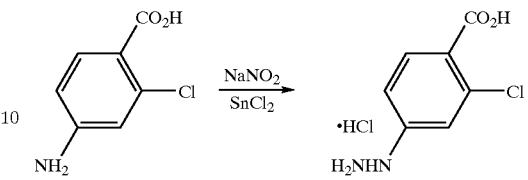

A solution of 5-amino-2-chlorobenzoic acid (10.3 g, 60 mmol) in concentrated HCl at 0° C. is treated with an aqueous solution of $NaNO_2$ (4.8 g, 70 mmol) at a rate to maintain a reaction temperature of <10° C., stirred for 0.5 h at 0° to 10° C., treated with a solution of tin chloride dihydrate (33.9 g, 150 mmol) in aqueous HCl at a rate to maintain a reaction temperature of <10° C., aqueous HCl is added periodically, as needed to facilitate stirring, stirred at 5° C. for an additional 1 h and filtered. The filtercake is recrystallized from water to afford the title product as white crystals, 9.6 g (71% yield), identified by HNMR analysis.

EXAMPLE 5

Preparation of 2-Chloro-5-{6-methyl-3-oxo-4-[3-(trifluoromethyl)phenyl]-3,6-dihydrodipyrazolo[3,4-b:3,4-d]pyrldin-2(1H)yl}benzoic acid

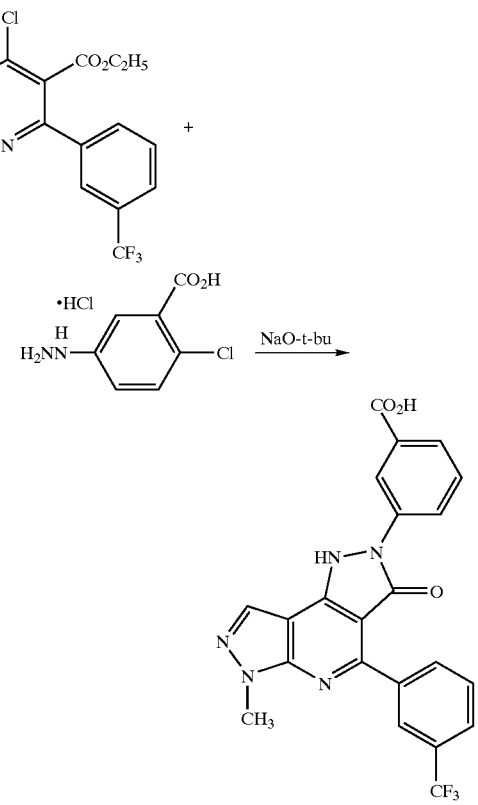

A solution of 2-chloro-5-hydrazinobenzoic acid hydrochloride (2.32 g, 10.4 mmol) in ethylene glycol is treated portionwise with NaO-t-bu (2.0 g, 20.8 mmol) at a rate to maintain a reaction temperature of <35° C. When addition is complete, the resultant solution is added to a solution of ethyl 4-chloro-1-methyl-6-[3-(trifluoromethyl)phenyl]-1H-pyrazolo[3,4-b]pyridine-5-carboxylate (2.0 g, 5.2 mmol) in ethylene glycol at 120° C., stirred at 125° C. for 15 h, cooled to room temperature, treated with additional NaO-t-bu (0.76 mg, 7.9 mmol), heated at 120° C. for 2–3 h, cooled to room temperature, quenched with dilute HCl (0.6N) and extracted with EtOAc. The extracts are combined, dried over $Na_2SO_4$ and concentrated in vacuo. The resultant residue is triturated in 1.25:1 EtOAc:$CH_3OH$ for 1 h at reflux temperature, cooled to room temperature and filtered. The filtercake is washed with 4:1 EtOAc:$CH_3OH$ and dried in vacuo to give the title product as a tan solid, 1.2 g (42% yield), mp 335.6–338° C., identified by HNMR and mass spectral analyses.

EXAMPLE 6

Preparation of 6-Methyl-2-[3-(4-morpholinylcarbonyl)phenyl]-1,6-dihydrodipyrazolo-[3,4-b:3,4-d]pyridin-3(2H)-one

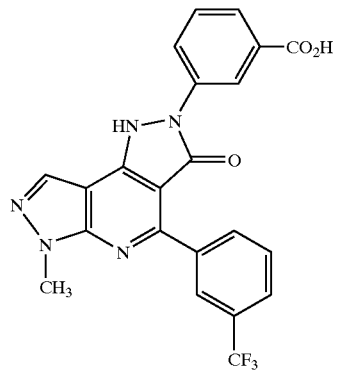

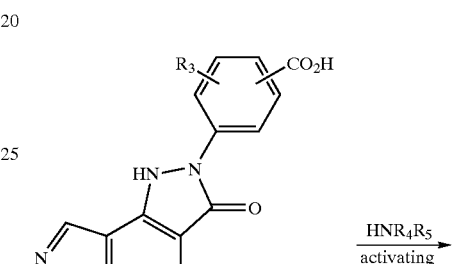

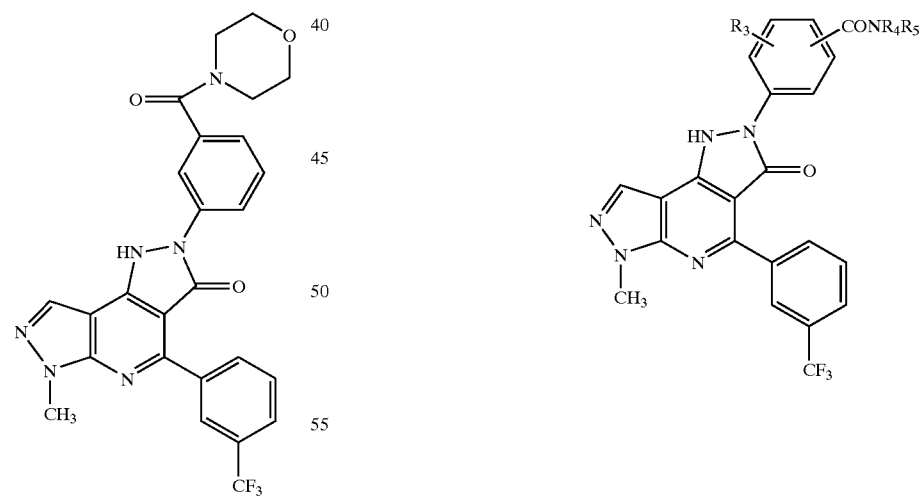

A solution of 3-{6-methyl-3-oxo-4-[3-(trifluoromethyl)phenyl]-3,6-dihydrodipyrazolo[3,4-b:3,4-d]pyridin-2(1H)-yl}benzoic acid (0.13 g, 0.29 mmol) in DMF is treated with 3 equivalents of morpholine, 3 equivalents of ethyldimethylaminocarbodiimide (EDC) HCL salt and 1.81 equivalents of diisopropyl ethyl amine, stirred at room temperature for 16 h, diluted with EtOAc and dilute (0.5N) HCl. The phases are separated and the organic phase is dried over $Na_2SO_4$ and concentrated in vacuo. The resultant residue is purified by flash chromatography (silica gel, 80:20, EtOAc:$C_2H_5OH$) to afford the title product as a yellow solid, 0.113 g (66% yield), mp 234.8° C. (dec), identified by HNMR and mass spectral analyses.

EXAMPLES 7–100

Preparation of Dihydrodipyrazolopyridinylbenzamide Compounds

Using essentially the same procedures described hereinabove and employing the desired benzoic acid substrate and appropriate amine, the compounds shown in Table I are obtained and identified by HNMR and mass spectral analyses: In Table I, the column headed CON designates the ring position of the amide function.

TABLE I

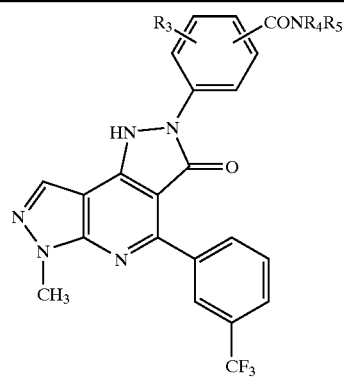

| Ex No. | R3 | CON | R4 | R5 | mp °C | % Yield |
|---|---|---|---|---|---|---|
| 7 | H | 3 | H | 4-hydroxyphenyl | — | 26 |
| 8 | H | 3 | CH₃ | CH₂CH(OCH₃)₂ | — | 70 |
| 9 | | 3 | | CH₂—S—CH₂CH₂ | 285–289 | 46 |
| 10 | H | 3 | | CH₂CH₂—S—CH₂CH₂ | — | 70 |
| 11 | H | 3 | | CH₂CH₂CH₂CH₂ | 255–258 | 36 |
| 12 | H | 3 | H | cyclopropylmethyl | — | 44 |
| 13 | H | 3 | | CH₂CH₂CH₂CH(CO₂H)—(2R) | 199–202 | 99 |
| 14 | H | 3 | CH₃ | CH₂CH₂—OH | — | 19 |
| 15 | H | 3 | | indole-3-carboxylic acid methyl ester | — | 54 |
| 16 | H | 3 | H | 4-aminobenzyl | 183(dec) | 12 |
| 17 | H | 3 | H | 4-hydroxy-3-methoxybenzyl | 172–176 | 45 |
| 18 | H | 3 | H | 3,4-dihydroxy-benzyl | 177.7–179.8 | 24 |
| 19 | H | 3 | H | CH₂CH(OH)CH₃ | — | 9.5 |
| 20 | H | 3 | H | CH₂CH₂—OCH₃ | — | 9.5 |
| 21 | 4-Cl | 3 | H | 3,4-dihydroxy-benzyl | 212–215 | 8.0 |
| 22 | 4-Cl | 3 | | CH₂CH₂CH₂CH(CO₂H)—(D) | 214–218 | 92 |
| 23 | 4-Cl | 3 | | CH₂CH₂CH₂CH(CH₂OH)—(2R) | — | 28 |
| 24 | 3-F | 4 | H | 3-(1-hydroxy-ethyl)phenyl | >350 | 52 |
| 25 | H | 4 | H | 3-(1-hydroxy-ethyl)phenyl | 251–254 | 68.3 |
| 26 | H | 4 | | CH₂CH₂CH(CO₂CH₃)CH₂CH₂ | 187(dec) | 45 |
| 27 | H | 4 | | CH₂CH₂N(CH₃)CH₂CH₂ | 191–194 | 45 |
| 28 | H | 4 | H | CH₂CH₂CH₂—OH | 193–195 | 42 |
| 29 | H | 4 | H | 3-(methoxy-methyl)phenyl | 210(dec) | 85 |
| 30 | 3-F | 4 | | CH₂CH₂OCH₂CH₂ | 176–179 | 78 |
| 31 | 3-F | 4 | H | 4-(2-hydroxyethyl)-phenyl | 185(dec) | 65 |
| 32 | H | 4 | H | benzyl | 189–192 | 83 |
| 33 | H | 4 | | CH₂CH₂OCH₂CH₂ | 287–290 | 65 |
| 34 | H | 4 | H | 4-(2-hydroxy-ethyl)phenyl | 186–189 | 72 |
| 35 | H | 4 | H | 3-(hydroxy-methyl)phenyl | 440(dec) | 85 |
| 36 | H | 4 | | CH₂CH₂CH₂CH(CH₂OH)CH₂ | 189.8–192.7 | 63 |
| 37 | H | 4 | H | 4-hydroxybutyl | 280(dec) | 40 |
| 38 | H | 4 | H | 3-acetylphenyl | 300(dec) | 15 |
| 39 | H | 4 | H | 5-aminopentyl | 234.5–236 | 20 |
| 40 | 3-Cl | 4 | | CH₂CH₂OCH₂CH₂ | 301–303.5 | 45 |
| 41 | 3-Cl | 4 | H | 3-(1-hydroxy-ethyl)phenyl | 326(dec) | 50 |
| 42 | H | 4 | H | 3-benzoic acid methyl ester | 220–222 | 27 |
| 43 | H | 4 | H | 5-hydroxy-5,6-7,8-tetrahydro-1-naphthalenyl | 298(dec) | 82 |
| 44 | H | 3 | H | NH₂ | — | 95 |
| 45 | H | 3 | H | CH₂CO₂CH₃ | — | 67 |
| 46 | H | 3 | H | CH₂CH₂OCH₂CH₂O—CH₂CH₂NH2 | — | 23 |
| 47 | H | 3 | H | 3,4-difluorophenyl | — | — |
| 48 | H | 3 | H | 3-benzoic acid ethyl ester | — | — |
| 49 | H | 3 | H | benzyl | — | — |

TABLE I-continued

| Ex No. | R3 | CON | R4 | R5 | mp °C. | % Yield |
|---|---|---|---|---|---|---|
| 50 | H | 3 | H | 3-(hydroxymethyl)-phenyl | — | — |
| 51 | H | 3 | H | 3-(1-hydroxyethyl)-phenyl | — | — |
| 52 | H | 3 | | 3,4-dihydro-2(1H)-isoquinoline | — | — |
| 53 | H | 3 | | CH₂CH₂CH₂CH(CO₂CH₃)—(2R) | — | — |
| 54 | H | 3 | | CH₂CH₂CH(CO₂H)CH₂CH₂ | — | — |
| 55 | H | 3 | H | 4-(2-hydroxy-ethyl)phenyl | — | — |
| 56 | H | 3 | CH₃ | benzyl | — | — |
| 57 | H | 3 | | CH₂CH₂CH₂CH(CH₃)CH₂ | — | — |
| 58 | H | 3 | | CH₂CH₂CH₂CH[CON(C₂H₅)₂]CH₂ | — | — |
| 59 | H | 3 | | CH₂CH₂CH(OH)CH₂CH₂ | — | — |
| 60 | H | 3 | H | 4-methoxybenzyl | — | — |
| 61 | H | 3 | CH₃ | CH₂CH₂CN | — | — |
| 62 | 4-F | 3 | H | 4(2-hydroxy-ethyl)phenyl | — | 53 |
| 63 | H | 3 | H | 3-methoxypropyl | — | — |
| 64 | 4-Cl | 3 | | CH₂CH₂CH₂CH(CO₂CH₃)—(D) | — | — |
| 65 | 4-F | 3 | H | 3-(1-hydroxy-ethyl)phenyl | — | 75 |
| 66 | 4-F | 3 | | CH₂CH₂OCH₂CH₂ | — | 48 |
| 67 | 4-F | 3 | H | 4-hydroxyphenyl | — | 65 |
| 68 | 4-F | 3 | H | 4-(hydroxy-methyl)phenyl | — | 78 |
| 69 | H | 3 | | CH₂CH₂CH₂CH(CO₂H)—(L) | 168–171 | 50 |
| 70 | H | 4 | H | H | — | 70 |
| 71 | H | 4 | H | 3-hydroxyphenyl | — | 66 |
| 72 | H | 4 | CH₃ | CH₂CH₂CN | — | 81 |
| 73 | H | 4 | H | 4-hydroxyphenyl | — | 45 |
| 74 | H | 4 | H | 2-hydroxyphenyl | — | 52 |
| 75 | H | 4 | H | cyclopropymethyl | — | 87 |
| 76 | H | 4 | H | 2-hydroxypropyl | — | 22 |
| 77 | H | 4 | | CH₂CH₂SCH₂CH₂ | — | 85 |
| 78 | H | 4 | H | 4-isopropylphenyl | — | 78 |
| 79 | H | 4 | H | 3-pyridyl | — | 35 |
| 80 | H | 4 | CH₃ | 2,2-dimethoxy-ethyl | — | 22 |
| 81 | H | 4 | | CH₂CH₂CH₂CH₂ | — | 78 |
| 82 | H | 4 | H | 3,4-difluorophenyl | — | 77 |
| 83 | H | 4 | | CH₂CH₂SCH₂ | — | 42 |
| 84 | H | 4 | H | 3-(hydroxymethyl-2-methylphenyl | — | 58 |
| 85 | H | 4 | CH₃ | 3-amino-3-oxo-propyl | — | — |
| 86 | H | 4 | H | 2-(hydroxy-methyl)phenyl | — | 53 |
| 87 | H | 4 | H | 4-(hydroxymethyl)-phenyl | — | 75 |
| 88 | H | 4 | | CH₂CH₂CH₂CH[CON(C₂H₅)₂]CH₂ | — | 61 |
| 89 | | 4 | H | 3-methoxypropyl | 160(dec) | 85 |
| 90 | H | 4 | H | 3-(dimethyl-amino)propyl | — | 30 |
| 91 | H | 4 | H | 4-fluorobenzyl | — | 68 |
| 92 | H | 4 | H | 3-aminobenzoic acid methyl ester | — | 41 |
| 92 | H | 4 | CH₃ | 2-hydroxyethyl | — | 33 |
| 94 | H | 4 | | CH₂CH₂CH(OH)CH₂CH₂ | — | 49 |

TABLE I-continued

| Ex No. | R3 | CON | R4 | R5 | mp °C. | % Yield |
|---|---|---|---|---|---|---|
| 95 | H | 4 | | CH₂CH₂CH₂CH(OH)CH₂ | — | 59 |
| 96 | H | 4 | H | 5-hydroxypentyl | — | 45 |
| 97 | H | 4 | H | 2-fluorobenzoic acid methyl ester | — | 73 |
| 98 | H | 4 | H | 3,4-dihydroxy-phenyl | 206–209 | 64 |
| 99 | 3-F | 4 | H | 4-hydroxyphenyl | — | 44 |
| 100 | H | 4 | H | 3-(1-hydroxy-propyl)phenyl | — | 65 |

EXAMPLE 101

Preparation of 4-{6-Methyl-3-oxo-4-[3-(trifluoromethyl)phenyl]-3,6-dihydrodipyrazolo[3,4-b:3',4'-d]pyridin-2-(1H)-yl}benzenesulfonamide

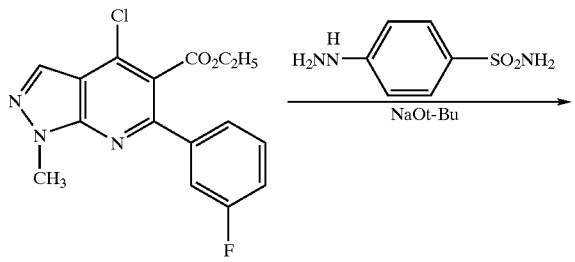

A solution of 4-aminosulfonylphenyl hydrazine dihydrochloride (0.87 g, 3.92 mmol) in ethanol is treated with NaO-t-Bu (0.37 g, 3.92 mmol), stirred at 70° C. for 20 min, treated with ethyl 4-chloro-1-methyl-6-[3-(trifluoromethyl)phenyl]-1H-pyrazolo[3,4-b]pyridine-5-carboxylate (0.5 g, 1.3 mmol) in ethanol, heated at reflux temperature for 6 days, cooled to room temperature, quenched with water, acidified to pH 3 with 3 NH and extracted with EtOAc. The extracts are combined, dried over Na₂SO₄ and concentrated in vacuo. The resultant residue is purified by flash chromatography (silica gel, 1:1 hexanes:EtOAc to afford the title compound as a white solid, 0.45 g (57% yield), mp 272–274° C., identified by HNMR and mass spectral analyses.

EXAMPLE 102

Preparation of N-(5-Hydroxypentyl)-4-{6-methyl-3-oxo-4-[3-(trifluoromethyl)phenyl]-3,6-dihydrodipyrazolo[3,4-b:3',4'-d]pyridin-2(1H)-yl}benzenesulfonamide

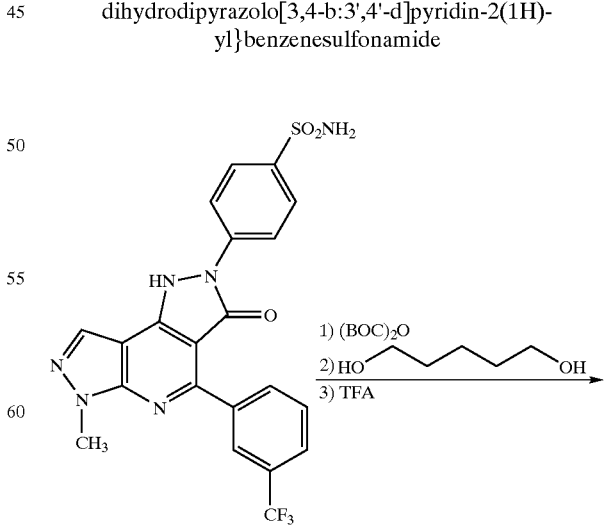

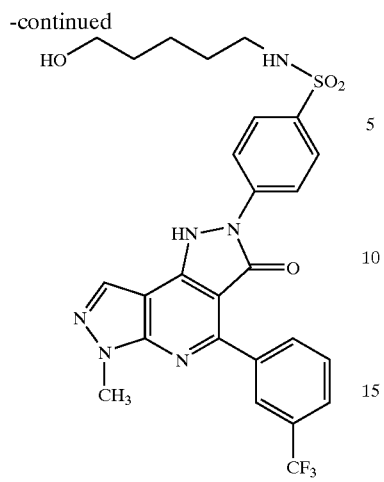

A solution of 4-{6-methyl-3-oxo-4-[3-(trifluoromethyl) phenyl]-3,6-dihydrodipyrazolo[3,4-b:3',4'-d]pyridin-2-(1H)-yl}benzenesulfonamide (2.78 mmol) in $CH_2Cl_2$ at 0° C. is treated with triethylamine (21.4 mmol) and di-t-butyl dicarbonate [(Boc)$_2$O] (3.87 mmol) in dimethylaminopyridine, allowed to warm to room temperature, diluted with water and extracted with $CH_2Cl_2$. The extracts are combined, dried over $Na_2SO_4$ and concentrated in vacuo. The resultant residue is flash chromatographed to afford the bis(t-butoxycarbonyl) intermediate in 51% yield. A solution of this intermediate (0.145 mmol) in THF is treated with pentane-1,5-diol (0.29 mmol), triphenyl phosphine (0.29 mmol) and diisopropylazodicarboxylate (0.261 mmol), stirred at room temperature for 16 h, poured into cold $NaHCO_3$ and extracted with EtOAc. The extracts are combined, dried over $Na_2SO_4$ and concentrated in vacuo to give a residue. This residue is chromatographed to afford the mono-Boc precursor to the title compound in 43% yield. This precursor (0.037 mmol) is treated with cold trifluoroacetic acid (0.2 mL), stirred at 0° C. for 40 min, diluted with water, treated with saturated $NaHCO_3$ to pH 8 and extracted with EtOAc. The extracts are combined, dried over $MgSO_4$ and concentrated in vacua. The resultant residue is flash chromatographed (silica gel, 100% EtOAc to 10% methanol in EtOAc gradient elution) to afford the title product as a white solid, 0.017 mmol (45% yield), identified by HNMR and mass spectral analyses.

EXAMPLES 103–107

Preparation of Dihydrodipyrazolopyridinylbenzenesulfonamide Compounds

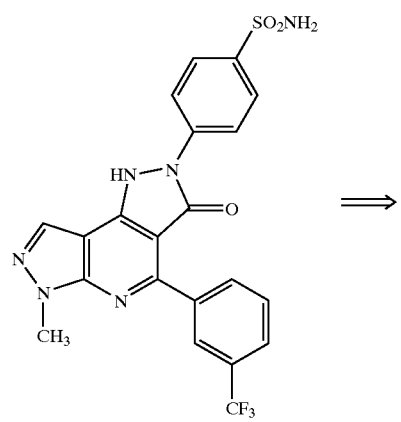

Using essentially the same procedure described in Example 102 hereinabove and employing the appropriate reagent, the compounds shown in Table II are obtained and identified by HNMR and mass spectral analyses.

TABLE II

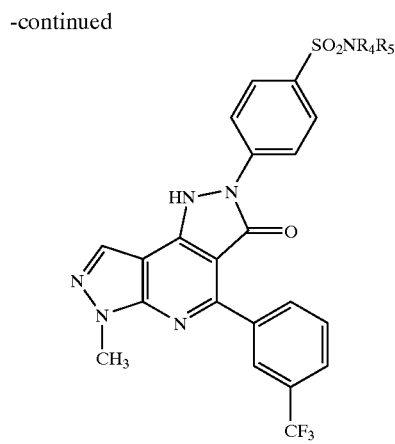

| Ex No. | R4 | R5 | % Yield |
|---|---|---|---|
| 103 | H | benzyl | 83 |
| 104 | H | 2-hydroxyethyl | 68 |
| 105 | H | $CH_2CO_2CH_3$ | 37 |
| 106 | H | cyclopropylmethyl | 16 |
| 107 | H | $CH_2CO_2H$ | 67 |

EXAMPLE 108

Evaluation of B7-1/CD28 Binding Inhibition for Test Compounds

CD28/B7-1 ELISA

Wells are coated with 300 ng CD28-Fc in carbonate buffer (pH 9.4) overnight at 4° C., blocked with 1% bovine serum albumin in tris-buffered saline (TBS) for 1 h at 22° C. and washed 3 times in TBS prior to assay. The detection complex is formed as follows: B7-1-Fc-biotin, prepared using NHS-LC-biotin (Pierce #21335) according to the manufacturers instructions (4.1 moles biotinimole Fc), is added at 0.8 ug/ml to streptavidin-alkaline phosphatase (Caltag Sa1008) at 1:1000 in TBS. A solution of test compound in dimethylsulfoxide (1% final) are added to this complex and incubated 30 min at 22° C. Detection complex (+/−inhibitors) is then added to the CD28 coated wells for 25 min at 22° C., washed 5 times with TBS, developed with the colorimetric substrate pNPP (Pierce #34045) in diethanolamine/$MgCl_2$ buffer (pH 9.5) and read at 405 nm. The inhibition constant ($IC_{50}$) is calculated by subtracting background binding and comparing to uninhibited (DMSO alone) controls. The inhibition constant represents the concentration of test compound required to achieve 50% inhibition. The results are shown in Table III.

TABLE III

| Example Number | B7-1/CD28 Inhibition IC50 (nM) |
|---|---|
| 6 | 54 |
| 7 | 38 |
| 8 | 31 |
| 9 | 53 |
| 10 | 70 |
| 11 | 44 |
| 12 | 80 |
| 13 | 20 |
| 14 | 61 |
| 15 | 63 |
| 16 | 57 |
| 17 | 55 |
| 18 | 9 |
| 19 | 45 |
| 20 | 62 |
| 21 | 22 |
| 22 | 44 |
| 23 | 43 |
| 24 | 110 |
| 25 | 3 |
| 26 | 90 |
| 27 | 500 |
| 28 | 98 |
| 29 | 110 |
| 30 | 310 |
| 31 | 64 |
| 32 | 79 |
| 33 | 13 |
| 34 | 23 |
| 35 | 17 |
| 36 | 180 |
| 37 | 88 |
| 38 | 44 |
| 39 | 140 |
| 40 | 84 |
| 41 | 550 |
| 42 | 94 |
| 43 | 300 |
| 44 | 80 |
| 45 | 100 |
| 46 | 150 |
| 47 | 280 |
| 48 | 440 |
| 49 | 120 |
| 50 | 100 |
| 51 | 130 |
| 52 | 300 |
| 53 | 270 |
| 54 | 860 |
| 55 | 110 |
| 56 | 180 |
| 57 | 92 |
| 58 | 110 |
| 59 | 105 |
| 60 | 180 |
| 61 | 330 |
| 62 | 380 |
| 63 | 180 |
| 64 | 180 |
| 65 | 1000 |
| 66 | 2400 |
| 67 | 280 |
| 68 | 370 |
| 69 | 100 |
| 70 | 38 |
| 71 | 140 |
| 72 | 110 |
| 73 | 11 |
| 74 | 17 |
| 75 | 107 |
| 76 | 50 |
| 77 | 140 |
| 78 | 120 |
| 79 | 180 |
| 80 | 170 |
| 81 | 110 |
| 82 | 120 |
| 83 | 110 |
| 84 | 90 |
| 85 | 1800 |
| 86 | 40 |
| 87 | 44 |
| 88 | 290 |
| 89 | 110 |
| 90 | 160 |
| 91 | 67 |
| 92 | 73 |
| 93 | 330 |
| 94 | 1200 |
| 95 | 390 |
| 96 | 92 |
| 97 | 640 |
| 98 | 36 |
| 99 | 31 |
| 100 | 800 |
| 102 | 670 |
| 103 | 1500 |
| 104 | 950 |
| 105 | 340 |
| 106 | 900 |
| 107 | 450 |

What is claimed is:

1. A compound of formula I

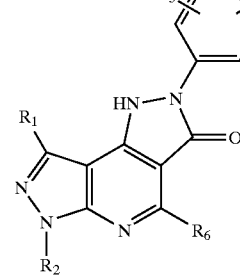

wherein

X is CO or $SO_2$;

$R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;

$R_3$ is H, F, Cl, Br or I;

$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group, phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group, benzyl optionally substituted with one or two halogen, $OR_{14}$, $COR_{18}$, or a $C_1$–$C_3$alkyl group optionally substituted with one $OR_{14}$ group, or pyridinyl optionally substituted with one or two halogen, $OR_{14}$, $NR_{15}R_{16}$ or $CO_2R_{17}$ groups, or $R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;

$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;

$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;

n is 0 or an integer of 1 or 2;

$R_{14}$ is H, $C_1$–$C_3$alkyl or $C_1$–$C_3$haloalkyl;

$R_{19}$ is H or $C_1$–$C_3$alkyl; and $R_{20}$ is a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted; or the stereoisomers thereof or the pharmaceutically acceptable salts thereof.

2. The compound according to claim 1 wherein X is CO.

3. The compound according to claim 1 wherein $R_1$ is H.

4. The compound according to claim 1 wherein $R_1$ is H, the compound according to claim 1 wherein $R_6$ is a phenyl group optionally substituted with one or two CN, $NO_2$, halogen, $CF_3$, $C_1$–$C_3$alkoxy or $CO_2R_{23}$ groups.

5. The compound according to claim 2 wherein $R_2$ is H or $C_1$–$C_3$alkyl.

6. The compound according to claim 2 wherein $R_4$ and $R_5$ are each independently H or a $C_1$–$C_3$alkyl, phenyl or benzyl group each optionally substituted with one or two hydroxy groups or $R_4$ and $R_5$ may be taken together with the atom to which they are attached to form a pyrrolidinyl or morpholinyl ring each optionally substituted with one carboxy group.

7. The compound according to claim 5 wherein $R_6$ is phenyl optionally substituted in the 3-position with $CF_3$.

8. The compound according to claim 7 wherein $R_1$ is H.

9. The compound according to claim 7 wherein $R_1$ is H, the compound according to claim 1 selected from the group consisting of:

N-(4-hydroxyphenyl)-3-(6-methyl-3-oxo-4-[3-(trifluoromethyl)phenyl]-3,6-dihydrodipyrazolo[3,4-b:3,4-d]pyridin-2(1H)-yl)benzamide;

N-(2,2-dimethoxyethyl)-N-methyl-3-(6-methyl-3-oxo-4-[3-(trifluoromethyl)phenyl]-3,6-dihydrodipyrazolo[3,4-b:3,4-d]pyridin-2(1H)-yl)benzamide;

6-methyl-2-[3-(1-pyrrolidinylcarbonyl)phenyl]-4-[3-(trifluoromethyl)phenyl]-1,6-dihydrodipyrazolo[3,4-b:3,4-d]pyridin-3(2H)-one;

(2R)-1-[3-(6-methyl-3-oxo-4-[3-(trifluoromethyl)phenyl]-3,6-dihydrodipyrazolo[3,4-b:3,4-d]-pyridin-2(1H)-yl)benzoyl]-2-pyrrolidinecarboxylic acid;

N-(3,4-dihydroxybenzyl)-3-(6-methyl-3-oxo-4-[3-(trifluoromethyl)phenyl]-3,6-dihydrodipyrazolo[3,4-b:3,4-d]pyridin-2(1H)-yl)benzamide;

N-(2-hydroxypropyl)-3-(6-methyl-3-oxo-4-[3-(trifluoromethyl)phenyl]-3,6-dihydrodipyrazolo[3,4-b:3,4-d]pyridin-2(1H)-yl)benzamide;

1-{2-chloro-5-[6-methyl-3-oxo-4-[3-(trifluoromethyl)phenyl]-3,6-dihydrodipyrazolo[3,4-b:3',4'-d]pyridin-2(1H)-yl]benzoyl}-D-proline;

2-(4-chloro-3-{[(2R)-2-(hydroxymethyl)pyrrolidin-1-yl]carbonyl}phenyl)-6-methyl-4-[3(trifluoromethyl)phenyl]-1,6-dihydrodipyrazolo[3,4-b:3,4-d]pyridin-3(2H)-one;

N-(4-hydroxyphenyl-4-{6-methyl-3-oxo-4-[3-(trifluoromethyl)phenyl]-3,6-dihydrodipyrazolo[3,4-b:3',4'-d]pyridin-2(1H)-yl}benzamide;

N-(2-hydroxyphenyl)-4-{6-methyl-3-oxo-3-[3-(trifluoromethyl)phenyl]-3,6-dihydrodipyrazolo[3,4-b:3',4'-d]pyridin-2(1H)-yl}benzamide;

6-methyl-2-[4-(4-morpholinylcarbonyl)phenyl]-4-[3-(trifluoromethyl)phenyl]-1,6-dihydrodipyrazolo[3,4-b:3,4-d]pyridin-3(2H)-one;

N-[4-(2-hydroxyethyl)phenyl]-4-(6-methyl-3-oxo-4-[3-(trifluoromethyl)phenyl]-3,6-dihydrodipyrazolo[3,4-b:3,4-d]pyridin-2(1H)-yl)benzamide;

N-[3-(1-hydroxyethyl)phenyl]-4-(6-methyl-3-oxo-4-[3-(trifluoromethyl)phenyl]-3,6-dihydrodipyrazolo[3,4-b:3,4-d]pyridin-2(1H)-yl)benzamide;

N-[3-(hydroxymethyl)pheny]-4-(6-methyl-3-oxo-4-[3-(trifluoromethyl)phenyl]-3,6-dihydrodipyrazolo[3,4-b:3,4-d]pyridin-2(1H)-yl)benzamide;

N-(5-hydroxypentyl)-4-(6-methyl-3-oxo-4-[3-(trifluoromethyl)phenyl]-3,6-dihydrodipyrazolo[3,4-b:3,4-d]pyridin-2(1H)-yl)benzenesulfonamide;

N-benzyl-4-[6-methyl-3-oxo-4-(3-trifluoromethyl-phenyl)-3,6-dihydro-1H-1,2,5,6,7-pentaaza-as-indacen-2-yl]-benzenesulfonamide;

N-(2-hydroxyethyl)-4-(6-methyl-3-oxo-4-[3-(trifluoromethyl)phenyl]-3,6-dihydrodipyrazolo[3,4-b:3,4-d]pyridin-2(1H)-yl)benzenesulfonamide;

methyl ({[4-(6-methyl-3-oxo-4-[3-(trifluoromethyl)pheny]-3,6-dihydrodipyrazolo[3,4-b:3,4-d]pyridin-2(1H)-yl)phenyl]sulfonyl}amino)acetate;

N-cyclopropylmethyl-4-[6-methyl-3-oxo-4-(3-trfluoromethyl-phenyl)-3,6-dihydro-1H-1,2,5,6,7-pentaaza-as-indacen-2-yl]-benzenesulfonamide;

({[4-(6-methyl-3-oxo-4-[3-(trifluoromethyl)phenyl]-3,6-dihydrodipyrazolo[3,4-b:3,4-d]pyridin-2(1H)-yl)phenyl]sulfonyl}amino)acetic acid;

the stereoisomers thereof; and the pharmaceutically acceptable salts thereof.

10. A method for the treatment of an immune disorder related to or affected by the immune regulatory protein B7-1 which comprises providing a patient in need thereof an immunotherapeutically effective amount of a compound of formula I

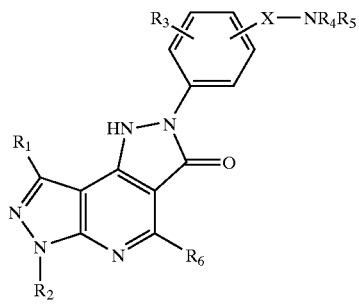

(I)

wherein
X is CO or $SO_2$;
$R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or
  phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;
$R_3$ is H, F, Cl, Br or I;
$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group,
  phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group,
  benzyl optionally substituted with one or two halogen, $OR_{14}$, $COR_{18}$, or a $C_1$–$C_3$alkyl group optionally substituted with one $OR_{14}$ group, or
  pyridinyl optionally substituted with one or two halogen, $OR_{14}$, $NR_{15}R_{16}$ or $CO_2R_{17}$ groups, or
$R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;
$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups,
  cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, or
  heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;
$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;
$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of
$R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;
n is 0 or an integer of 1 or 2;
$R_{14}$ is H, $C_1$–$C_3$alkyl or $C_1$–$C_3$haloalkyl;
$R_{19}$ is H or $C_1$–$C_3$alkyl; and
$R_{20}$ is a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted; or
the stereoisomers thereof or the pharmaceutically acceptable salts thereof.

11. The method according to claim 10 wherein said disorder is transplant rejection.

12. The method according to claim 10 wherein said disorder is an autoimmune disease.

13. The method according to claim 10 wherein said disorder is graft vs. host disease.

14. The method according to claim 12 wherein said disease is multiple sclerosis or rheumatoid arthritis.

15. A pharmaceutical composition which comprises a pharmaceutically acceptable carrier and an effective amount of a compound of formula I

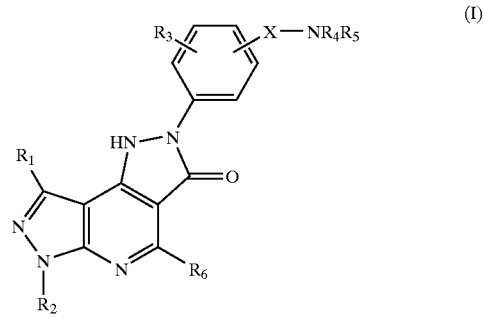

(I)

wherein
X is CO or $SO_2$;
$R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or
  phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;
$R_3$ is H, F, Cl, Br or I;
$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group,
  phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group,
  benzyl optionally substituted with one or two halogen, $OR_{14}$, $COR_{18}$, or a $C_1$–$C_3$alkyl group optionally substituted with one $OR_{14}$ group, or
  pyridinyl optionally substituted with one or two halogen, $OR_{14}$, $NR_{15}R_{18}$ or $CO_2R_{17}$ groups, or
$R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;
$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;

$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;

n is 0 or an integer of 1 or 2;

$R_{14}$ is H, $C_1$–$C_3$alkyl or $C_1$–$C_3$haloalkyl;

$R_{19}$ is H or $C_1$–$C_3$alkyl; and $R_{20}$ is a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted; or the stereoisomers thereof or the pharmaceutically acceptable salts thereof.

16. The composition according to claim 15 having a formula I compound wherein X is CO.

17. The composition according to claim 16 having a formula I compound wherein $R_1$ is H.

18. The composition according to claim 17 having a formula I compound wherein $R_2$ is H or $CH_3$.

19. The composition according to claim 18 having a formula I compound wherein $R_6$ is phenyl optionally substituted in the 3-position with $CF_3$.

20. A process for the preparation of a compound of formula Ia

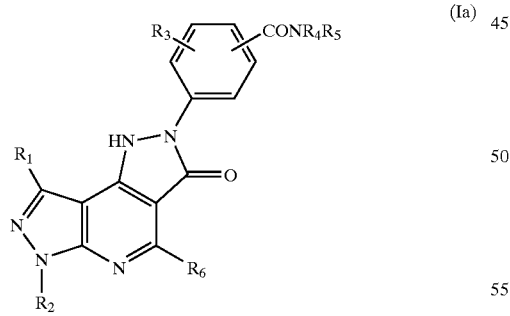

(Ia)

wherein $R_1$ and $R_2$ are each independently H, $C_1$–$C_{10}$alkyl optionally substituted with one or more halogen, hydroxy, $C_1$–$C_4$alkoxy, $CO_2R_8$, $CONR_9R_{10}$, $C_3$–$C_7$cycloalkyl or optionally substituted phenyl groups, or phenyl optionally substituted with one to three halogen, hydroxy, $C_1$–$C_6$haloalkyl, $C_1$–$C_4$alkoxy, $CO_2R_{11}$, $NR_{12}R_{13}$ or CN groups;

$R_3$ is H, F, Cl, Br or I;

$R_4$ and $R_5$ are each independently H, $NH_2$, $CH_2CH_2OCH_2CH_2OCH_2CH_2NH_2$ or a $C_1$–$C_6$alkyl group optionally substituted with one or two CN, $OR_{14}$, $NR_{15}R_{16}$, $CO_2R_{17}$ or $C_3$–$C_7$cycloalkyl group, phenyl optionally substituted with one or two halogen, CN, $OR_{14}$, $NR_{15}R_{16}$, $CO_2R_{17}$, $COR_{18}$, an optionally substituted $C_1$–$C_6$alkyl or an optionally substituted $C_2$–$C_6$alkenyl group, benzyl optionally substituted with one or two halogen, $OR_{14}$, $COR_{18}$, or a $C_1$–$C_3$alkyl group optionally substituted with one $OR_{14}$ group, or pyridinyl optionally substituted with one or two halogen, $OR_{14}$, $NR_{15}R_{16}$ or $CO_2R_{17}$ groups, or $R_4$ and $R_5$ may be taken together with the atom to which they are attached to form an optionally substituted 5- to 7-membered ring optionally containing one double bond, a benzofused ring or an additional heteroatom selected from O, $NR_{19}$ or S;

$R_6$ is phenyl optionally substituted with one to three halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, cycloheteroalkyl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups, or heteroaryl optionally substituted with one or more halogen, $NO_2$, CN, hydroxy, $C_1$–$C_6$alkyl, $C_1$–$C_6$alkylthio, $C_1$–$C_6$haloalkyl, $C_1$–$C_6$alkoxy, phenyl, phenoxy, benzyl, benzyloxy, $SO_nR_{20}$, $SO_2NR_{21}R_{22}$, $CO_2R_{23}$ or $NR_{24}R_{25}$ groups;

$R_8$, $R_{11}$, $R_{17}$, $R_{18}$ and $R_{23}$ are each independently H or a $C_1$–$C_6$alkyl, $C_3$–$C_7$ cycloalkyl, $C_1$–$C_6$haloalkyl, phenyl, $C_5$–$C_7$cycloheteroalkyl or heteroaryl group each optionally substituted;

$R_9$, $R_{10}$, $R_{12}$, $R_{13}$, $R_{15}$, $R_{16}$, $R_{21}$, $R_{22}$, $R_{24}$ and $R_{25}$ are each independently H or a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted or each of $R_9$ and $R_{10}$ or $R_{12}$ and $R_{13}$ or $R_{15}$ and $R_{16}$ or $R_{21}$ and $R_{22}$ or $R_{24}$ and $R_{25}$ may be taken together with the nitrogen atom to which they are attached to form a 5- to 7-membered ring optionally containing another heteroatom selected from O, N or S;

n is 0 or an integer of 1 or 2;

$R_{14}$ is H, $C_1$–$C_3$alkyl or $C_1$–$C_3$haloalkyl;

$R_{19}$ is H or $C_1$–$C_3$alkyl; and $R_{20}$ is a $C_1$–$C_6$alkyl, $C_3$–$C_7$cycloalkyl, $C_1$–$C_6$haloalkyl, phenyl, $C_5$–$C_7$cycloheteroalkyl or heteroaryl group each optionally substituted which process comprises reacting a compound of formula II

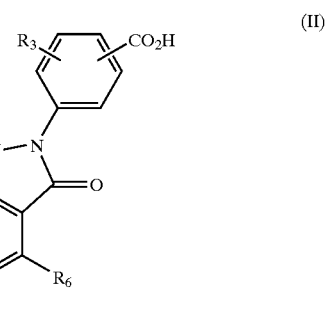

(II)

wherein $R_1$, $R_2$, $R_3$ and $R_6$ are defined hereinabove with an amine, $HNR_4R_5$, in the presence of an activating agent and a solvent.

* * * * *